US00PP20060P3

(12) United States Plant Patent
Hambali et al.

(10) Patent No.: US PP20,060 P3
(45) Date of Patent: Jun. 9, 2009

(54) ***CALATHEA* PLANT NAMED 'TWYCA0019 2'**

(50) Latin Name: ***Calathea* hybrid**
Varietal Denomination: TWYCA0019 2

(75) Inventors: Gregori Garnadi Hambali, Bogor (ID); Marianne E. Knauss, Longwood, FL (US)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 75 days.

(21) Appl. No.: 11/894,578

(22) Filed: Aug. 21, 2007

(65) Prior Publication Data

US 2009/0055985 P1 Feb. 26, 2009

(51) Int. Cl.
*A01H 5/00* (2006.01)

(52) U.S. Cl. ..... Plt./375

(58) Field of Classification Search ..... Plt./375
See application file for complete search history.

(56) References Cited

U.S. PATENT DOCUMENTS

PP9,621 P * 8/1996 Lamb ..... Plt./375
PP16,028 P2 * 10/2005 Hambali ..... Plt./375

* cited by examiner

*Primary Examiner*—Wendy C. Haas
(74) *Attorney, Agent, or Firm*—Jondle & Associates, P.C.

(57) ABSTRACT

A new *Calathea* plant particularly distinguished by having pink and green bracted inflorescences which are held high above the foliage, sturdy and upright growth habit, large, ovate to elliptical leaves with dark green margins and broad grey-green elliptical centers, is disclosed.

1 Drawing Sheet

Genus and species: *Calathea* hybrid.
Variety denomination: 'TWYCA0019 2'.

BACKGROUND OF THE NEW PLANT

The present invention comprises a new and distinct cultivar of *calathea,* botanically known as *Calathea* hybrid and hereinafter referred to by the cultivar name 'TWYCA0019 2'. The new cultivar originated as a sport from a *Calathea* plant designated 'Indri' (U.S. Plant No. 16,028) in the Spring of 2005 in Apopka, Fla.

A single plant selection was chosen for further evaluation and for asexual propagation in Spring, 2005.

The new cultivar was first propagated in the Summer of 2005 in Apopka, Fla. and has been asexually reproduced repeatedly by division and tissue culture over two generations. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Tall, upright branching habit;
2. Pink and green bracted inflorescences which are held above the foliage;
3. Large ovate to elliptical medium green leaves with silver-green markings.

DESCRIPTION OF PHOTOGRAPH

This new *Calathea* plant is illustrated by the accompanying photograph which shows the overall plant habit including blooms and foliage of the plant; the colors shown are as true as can be reasonably obtained by conventional photographic procedures.

DESCRIPTION OF THE NEW CULTIVAR

The following detailed description sets forth the distinctive characteristics of 'TWYCA0019 2'. The data which define these characteristics were collected from asexual reproductions carried out in Apopka, Fla. The data were obtained in August 2006 from 12-month old plants grown in 6-inch pots from a 13-week-old tissue-culture derived liner. The plants were grown in a greenhouse with average daily temperatures of 24° C.–35° C. and average nightly temperatures of 18° C.–95° C. Color readings were taken under natural light in the greenhouse. Color references are to The Royal Horticultural Society Colour Chart, 2001 edition.

DETAILED BOTANICAL DESCRIPTION OF THE NEW PLANT

Classification:
- *Family.*—Marantaceae.
- *Botanical name.*—*Calathea* hybrid.
- *Common name.*—*Calathea.*

Parentage:
- *Mutation parent.*—'Indri' *Calathea* hybrid (U.S. Plant Pat. No. 16,028).

Growth:
- *General.* —Tropical flowering potted plant; plant is suitable for use in shaded tropical landscapes.
- *Time to flower.*—12 months to flowering, starting from a 13-week old liner from tissue culture.
- *Appropriate container.*—15 cm to 20 cm pots; suitable for use in shaded tropical landscapes and indoors.

Plant description:

*Life cycle.*—Herbaceous perennial.

*Habit.*—Upright, wider than tall, inverted triangle, densely leafy; inflorescences upright and held above and among the foliage in the center of the plant; upright whorls of leaves arise from underground rhizome; rhizomaceous.

*Vigor.*—Typical of *Calathea;* progressive and consistent growth.

*Height.*—28.0 cm to 35.0 cm.

*Spread* (*including flowers*).—49.0 cm to 57.0 cm.

*Root color.*—RHS N199B (Brown); tips RHS 145D to RHS 155A.

Branches:

*Branching habit.*—Basal branching, rhizomaceous.

*Number.*—10 basal branches.

*Length.*—Variable depending upon age.

*Lateral branch diameter.*—1.2 cm.

Stems (rhizomes):

*Description.*—Cylindrical, round in traverse section.

*Aspect.*—Horizontal, underground rhizome becoming upturned, vertical at tip.

*Strength.*—Thick, tough and fibrous.

*Internode length.*—0.9 cm to 2.5 cm.

*Color.*—RHS N170C to RHS N170D.

Leaves:

*Arrangement.*—Alternate, closely spaced in vertical ranks, rosette, with one to four leaves per lateral branch depending on age of the branch.

*Shape.*—Simple, elliptical.

*Apex.*—Cuspidate.

*Base.*—Obtuse.

*Margin.*—Entire, wavy.

*Size.*—Length: 16.0 cm to 20.0 cm. Width: 11.0 cm to 13.0 cm.

*Color.*—Immature leaf: Upper surface: Leaf margin of RHS 147A to RHS 146A (Medium-green) with a broad diffuse band of two shades of RHS 194B (Silver-green) and RHS 147B to RHS 147C; RHS 147A to 146A (Medium green) in the center; RHS 146A to 146B (Pale-green) markings following the mid-rib. Lower surface: RHS 191A. Mature leaf: Upper surface: Leaf margin RHS 147A (Green) with a broad diffuse band of two shades of RHS 194B to RHS 194C (Silver-green) and RHS 147B; Leaf center of RHS 147A (Medium-green); RHS 146A to RHS 146B (Pale green) markings following the mid-rib. Lower surface: RHS 191A to RHS 147B.

*Venation.*—Type: Pinnate. Color: Upper surface: Midrib: RHS 147B tinged with RHS 199B. Primary veins: RHS 147A. Lower surface: Midrib: RHS 199A to RHS 199B. Primary veins: RHS 191A to RHS 147B.

*Texture.*—Upper surface: Glossy to shiny, concave between primary veins resulting in a slightly textured look. Lower surface: Matte, dull.

*Surface pubescence.*—Absent.

Petiole:

*Length.*—19.0 cm to 24.0 cm.

*Diameter.*—0.5 cm.

*Texture.*—Smooth.

*Color.*—RHS 148A tinged with RHS 199B.

*Petiole sheath.*—Encircles the rhizome and extends up the petiole to within 8.0 cm of the base of the leaf.

*Color.*—Outside: RHS 146A tinged with RHS 199B and flushed with RHS N170D. Inside: Smooth, shiny RHS 146B tinged with RHS 199B.

*Cataphylls.*—Shape: Lanceolate. Apex: Acute. Base: Sessile, clasping rhizome. Length: 10.0 cm to 12.0 cm. Diameter (flattened): 2.0 cm. Color: Outside: RHS 146A tinged with RHS 199B and flushed with RHS N170D. Inside: Smooth, shiny RHS 146B tinged with RHS 199B. Texture: Outside covered with short, fine pubescence.

Geniculum:

*General.*—The orientation of the leaf to the petiole is variable, as the geniculum bends. During the night and early morning the geniculum is straight, and the leaf is held nearly vertical above the foliage. During the day, the geniculum is bent, and the leaf is held about 90° to the petiole.

*Length.*—3.2 cm.

*Diameter.*—0.5 cm.

*Color.*—RHS 199A to RHS 148A.

Flower bud:

*Texture.*—Smooth.

*Size.*—Length: 2.0 cm. Diameter: 0.35 cm.

*Shape.*—Elongated, elliptical.

*Color.*—Translucent white.

Inflorescence:

*Lastingness of the flowers on the plant.*—Individual flowers last about one day before shrivelling.

*Flowering season.*—Spring and fall 1 to 3 flowers may open simultaneously per inflorescence per day over a period of about 8 weeks.

*Arrangement.*—Inflorescence emerges from the center of the whorl of leaves. Flowers emerge from short branch spikes under colourful bracts atop a tall upright spike.

*Inflorescence type.*—Tall, upright, terminally bracted spike; bracts arranged in closely spaced vertical ranks occupying the upper 6.0 cm of the spike.

*Inflorescence height.*—30.0 cm to 36.0 cm.

*Inflorescence width.*—7.0 cm from tip to tip of bracts across top of inflorescence.

*Number of flowers per inflorescence.*—72.

*Quantity of flowers and buds per plant.*—11 spikes present; about 440 flowers and buds per plant.

*Fragrance.*—Absent.

*Flowering habit.*—Tips of petals and staminods emerge from branch spikes under fertile bracts; flowers last about one day before fading and shrivelling.

Flowers:

*Form.*—Tube-like.

*General.*—Self-cleaning.

*Shape.*—Tube like; staminodes and petals curve outward.

*Diameter.*—1.8 cm across the face of the flower; tube of flower is 0.3 cm.

*Petals.*—General: 3 petals per flower; tube-like with a translucent, delicate appearance that curves outward at the tips. Size: Length: 3.2 cm. Width: 0.5 cm. Shape: Narrow, elliptic Apex: Acute. Margin: Entire. Texture: Smooth, both surfaces. Aspect: Outward. Color (both surfaces): Translucent white, fading to RHS 199C to RHS 199D, ultimately becoming RHS 200A.

Sepals:

*General.*—Composed of 3 sepals; translucent, pale white, crystalline with a tube-like arrangement.

*Shape.*—Narrow elliptic to linear.

*Apex.*—Acute.

*Base.*—Acute.

*Margin.*—Entire.
*Length.*—2.2 cm.
*Width.*—0.4 cm.
*Texture.*—Both sides are smooth.
*Color (both surfaces).*—RHS 155D (Translucent white).

Peduncle:
*Length.*—30.0 cm to 36.0 cm.
*Diameter.*—0.5 cm.
*Angle.*—Straight upright.
*Strength.*—Tough flexible.
*Texture.*—Smooth.
*Color.*—RHS 148A tinged with RHS 199B.

Bracts:
*General.*—Terminal bracts uppermost on raceme, subtended by fertile bracts with underlying branch spikes.
*Terminal bracts.*—Quantity: 8. Length: 4.0 cm. Width: 2.0 cm. Shape: Elliptic, flat or reflexed. Apex: Acute. Base: Acute. Margin: Entire, smooth. Color: Upper surface: Margin RHS 186A to RHS 186B (Pink); edge tinged with RHS 186D; Center RHS 138B to RHS 138D. Lower surface: RHS 194B to RHS 194C tinged with RHS 199A; margins are RHS 186A to RHS 186B. Texture: Upper surface: Smooth. Lower surface: Slightly rough.
*Fertile bracts.*—Quantity: 11. Length: 2.8 cm. Width: 3.3 cm. Shape: Broadly obovate. Apex: Emarginate. Base: Acute. Margin: Entire, smooth. Color: Upper surface: Margins are RHS 186C to RHS 186 D with the center RHS 191B to RHS 191C. Lower surface: Margins are RHS 186B to RHS 186C, with the center RHS 138B. Texture: Upper surface: Smooth. Lower surface: Slightly rough.

Reproductive organs:
*Staminode.*—3; thin, crystalline, delicate, with a tube-like arrangement that is flared outward and reflexed at the tips. Shape: Two are spatulate with emarginated tips, one is short reduced, linear, cupped at the tip. Margin: Entire. Length: 3.2 cm; reduced staminode is 2.7 cm. Width: 0.8 cm at widest point; reduced staminode is 0.3 cm. Texture (both surfaces): Smooth. Color: Spatulate staminodes translucent white RHS 155B flushed with RHS N87C; reduced staminodes are translucent white, RHS 155B flushed with RHS N87C.
*Stamens.*—Quantity: 1. Anther shape: Lanceolate. Anther length: 0.1 cm. Anther width: 0.05 cm. Anther color: RHS 8C (Yellow). Pollen Amount: Sparse. Color: RHS 155A.
*Pistils.*—Quantity: 1. Length: 2.9 cm. Stigma shape: Elliptic, cupped. Stigma color: RHS 155A (White). Style length: 2.9 cm. Style diameter: 0.1 cm. Style color: RHS 155A (White). Ovary: Inferior, 3 celled. Color: RHS 155A (White). Length: 0.22 cm. Width: 0.19 cm.

Fruit and seed set: Has not been observed.

Disease and insect resistance: Resistance and susceptibility is typical of the species.

COMPARISON WITH PARENTAL AND COMMERCIAL CULTIVARS

'TWYCA0019 2' differs from the mutation parent *Calathea* hybrid 'Indri' (U.S. Plant Pat. No. 16,028) in that 'TWYCA0019 2' has a lower leaf surface that is green colored, while 'Indri' has a lower leaf surface that is purple colored.

'TWYCA0019 2' differs from the commercial variety *Calathea* named 'Eclipse' (U.S. Plant Pat. No. 9,621) in that 'TWYCA0019 2' has green colored lower leaf surface, while 'Eclipse' has a lower leaf surface with a dark purple color. 'TWYCA0019 2' has long lasting pink and green bracted inflorescences which are displayed above the foliage, while 'Eclipse' has green bracted inflorescences that are short scaped, inconspicuous and held among and below the foliage. 'TWYCA0019 2' is taller and has a more upright growth habit, while 'Eclipse' has a shorter, more spreading growth habit. Additionally, 'TWYCA0019 2' has large leaves, while 'Eclipse' has small leaves.

I claim:

1. A new and distinct cultivar of *Calathea* plant as shown and described herein.

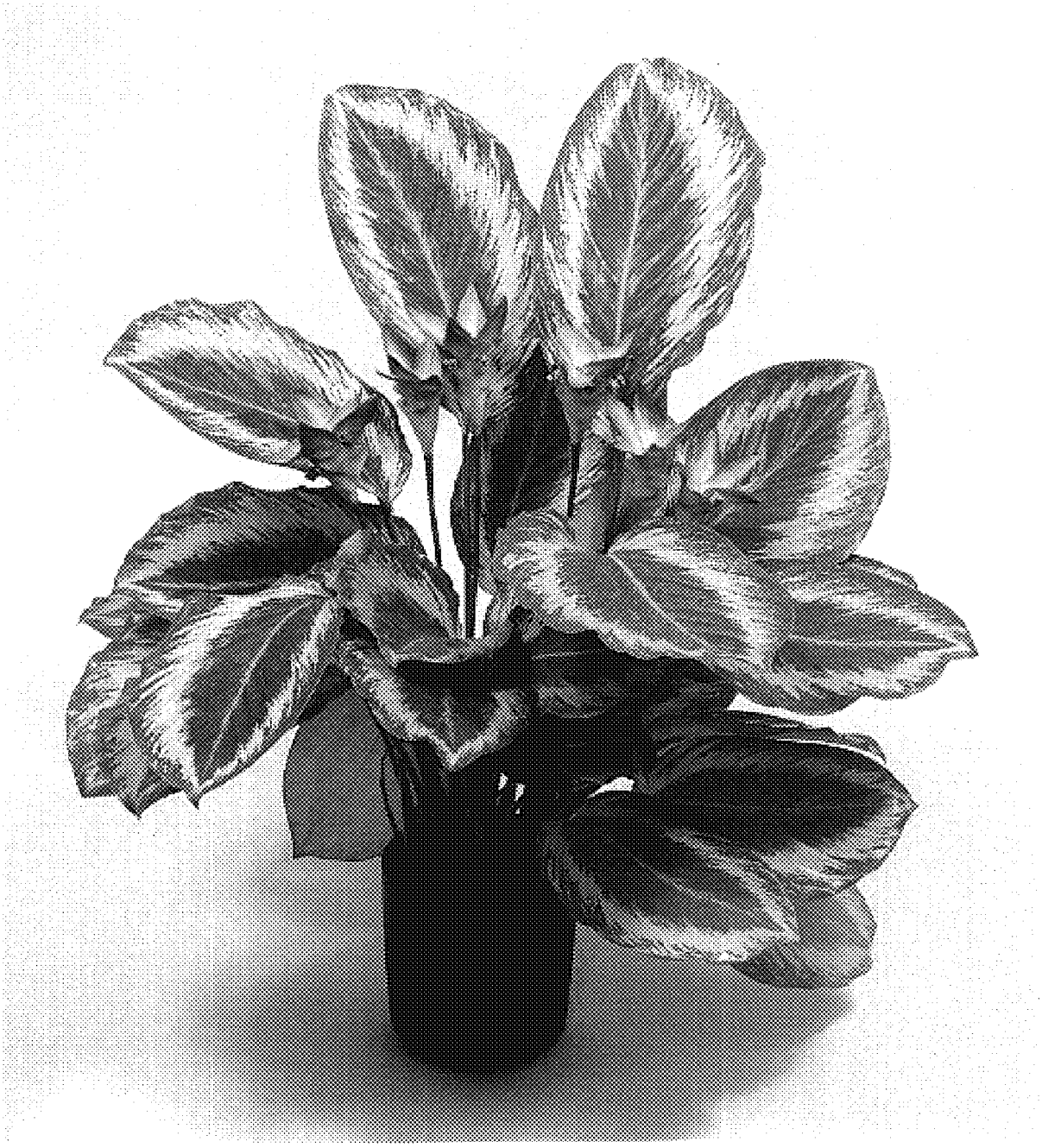

* * * * *